US009808155B2

(12) United States Patent
Verdooner (10) Patent No.: US 9,808,155 B2
(45) Date of Patent: Nov. 7, 2017

(54) APPARATUS TO DETECT AMYLOID IN A PATIENT USER'S RETINA IN A DIAGNOSIS, ADVANCEMENT AND PROGNOSIS OF ALZHEIMER'S DISEASE, TRAUMATIC BRAIN INJURY, MACULAR DEGENERATION AND A PLURALITY OF NEURODEGENERATIVE DISORDERS AND OCULAR DISEASES

(71) Applicant: NeuroVision Imaging LLC, Sacramento, CA (US)

(72) Inventor: Steven Roger Verdooner, Granite Bay, CA (US)

(73) Assignee: NeuroVision Imaging LLC, Sacramento, CA (US)

( * ) Notice: Subject to any disclaimer, the term of this patent is extended or adjusted under 35 U.S.C. 154(b) by 174 days.

(21) Appl. No.: 14/191,401

(22) Filed: Feb. 26, 2014

(65) Prior Publication Data

US 2014/0176908 A1 Jun. 26, 2014

Related U.S. Application Data (63) Continuation-in-part of application No. 13/280,161, filed on Oct. 24, 2011, now abandoned.

(60) Provisional application No. 61/406,551, filed on Oct. 25, 2010.

(51) Int. Cl.
*A61B 3/10* (2006.01)
*A61B 3/13* (2006.01)
*A61B 5/00* (2006.01)

(52) U.S. Cl.
CPC .............. *A61B 3/13* (2013.01); *A61B 3/10* (2013.01); *A61B 3/102* (2013.01); *A61B 5/0042* (2013.01); *A61B 5/0066* (2013.01); *A61B 5/4064* (2013.01)

(58) Field of Classification Search
CPC ......... A61B 3/102; A61B 3/12; A61B 3/1208; A61B 3/1233; A61B 3/1241; A61B 3/13; A61B 3/14; A61B 3/145
USPC .......................... 351/205, 206, 210, 218, 221
See application file for complete search history.

(56) References Cited

U.S. PATENT DOCUMENTS

| 7,854,510 | B2 | 12/2010 | Verdooner |
| 8,025,406 | B2 | 9/2011 | Zhang |
| 2003/0184712 | A1 * | 10/2003 | Takeda ................. A61B 3/0033 351/245 |
| 2005/0094102 | A1 | 5/2005 | Cornsweet |
| 2005/0134796 | A1 | 6/2005 | Zelvin |
| 2005/0214222 | A1 | 9/2005 | McKinnon |

(Continued)

FOREIGN PATENT DOCUMENTS

WO 2010033861 A1 3/2010

*Primary Examiner* — Huy K Mai
(74) *Attorney, Agent, or Firm* — Lucas & Mercanti, LLP; Peter J. Phillips (57) ABSTRACT

An eye imaging apparatus to produce an image of an eye of a patient user is disclosed. The eye imaging apparatus may include a video camera, a slit lamp chinrest, a camera housing, a plurality of illumination source optics and a processing system. The eye imaging apparatus may also include a video camera, a plurality of video camera optics, a camera housing, a microscope assembly, a plurality of illumination source optics and a floor base. The eye imaging apparatus may be utilized in combination with one or more contrasting agents. The eye imaging apparatus may detect amyloid-beta plaque, amyloid or amyloid-beta peptide by a spectral signature.

20 Claims, 7 Drawing Sheets (56) References Cited

U.S. PATENT DOCUMENTS

| | | | |
|---|---|---|---|
| 2006/0215113 A1* | 9/2006 | Chernyak | A61B 3/11 351/246 |
| 2007/0270350 A1* | 11/2007 | Singh | A61K 45/06 514/1.4 |
| 2008/0188737 A1 | 8/2008 | Assmann | |
| 2009/0096988 A1 | 4/2009 | Fink | |
| 2010/0033676 A1* | 2/2010 | De Vries | A61B 3/102 351/206 |
| 2010/0097573 A1 | 4/2010 | Verdooner | |
| 2010/0259725 A1 | 10/2010 | Siminou | |
| 2011/0234977 A1 | 9/2011 | Verdooner | |
| 2011/0286932 A1 | 11/2011 | Koronyo | |
| 2012/0101371 A1 | 4/2012 | Verdooner | |
| 2014/0009740 A1* | 1/2014 | Makino | A61B 3/14 351/206 |

\* cited by examiner

APPARATUS TO DETECT AMYLOID IN A PATIENT USER'S RETINA IN A DIAGNOSIS, ADVANCEMENT AND PROGNOSIS OF ALZHEIMER'S DISEASE, TRAUMATIC BRAIN INJURY, MACULAR DEGENERATION AND A PLURALITY OF NEURODEGENERATIVE DISORDERS AND OCULAR DISEASES

The present application is a Continuation-In-Part application of U.S. Non-Provisional application Ser. No. 13/280,161 filed on Oct. 24, 2011. The present application claims priority to U.S. Provisional Application 61/406,551 filed on Oct. 25, 2010, the entire of both disclosures are incorporated by reference herein.

TECHNICAL FIELD & BACKGROUND

Imaging of amyloid-beta plaques including amyloid, amyloid-beta peptides and other pathology and anatomical features in a patient user's retina or a patient user's brain is often unobtainable without the utilization of specialized contrast agents or autofluorescence techniques. While drusen and amyloid containing plaques may be visible in the patient user's retina with a variety of imaging techniques, specifically amyloid beta plaques, including amyloid in other forms such as amyloid peptides, located in drusen or other amyloid containing plaques or in the patient user's retina or fundus at large, may not be visible and verifiable as containing amyloid with any retinal imaging modalities with the sole exception of curcumin fluorescence reflectance imaging that has been performed in vivo in animals only.

SUMMARY OF THE INVENTION

The eye imaging apparatus may be utilized to detect amyloid in the patient user's retina and the patient user's brain. This may be achieved solely with Optical Coherence Tomography or OCT by identification of a spectral signature of an amyloid in an OCT data set and/or the anatomic location of plaques. The detection may also be achieved by varying the wavelength of the OCT device and analyzing a generated signal to derive an amyloid signal. This may also be achieved by a combination of OCT with multispectral imaging or the utilization of multispectral imaging alone or the utilization of autofluorescence or a contrast agent together with OCT. In each of the modalities, a spectral signature may be obtained by spectral analysis and image processing. The image processing may identify the spectral wavelength and the spectral signature identified with amyloid in the patient user's retina and the patient user's brain utilizing the image processing techniques.

The eye imaging apparatus utilizes a plurality of OCT and current fundus imaging techniques to visualize amyloid in the patient user's retina or the patient user's brain through a combination of optical technology in combination with spectral analysis and image processing. By operating a plurality of OCT and multispectral imaging devices at a plurality of specific wavelengths, a spectral signature of amyloid-beta plaques may be allowed to be obtained from a data set utilizing image processing.

The eye imaging apparatus utilizes a plurality of different operating modes and configurations such as a hand-held instrument or a mounted slit lamp, an integrated slit lamp, an integrated fundus camera, a scanning laser ophthalmoscope or an optical head such as a fundus camera coupled to a separate chinrest-joystick assembly.

The eye imaging apparatus utilizes OCT and/or multispectral imaging in combination with standard or proprietary spectral wavelength selection, spectral analysis and image processing to identify amyloid in a patient user's retina or a patient user's brain rendering it visible to a clinician user.

BRIEF DESCRIPTION OF THE DRAWINGS

The present invention will be described by way of exemplary embodiments, but not limitations, illustrated in the accompanying drawings in which like references denote similar elements, and in which.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations may be set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention. However, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

FIG. 1 A illustrates a side view of an eye imaging apparatus 100, in accordance 20 with one embodiment of the present invention. The eye imaging apparatus 100 may include a video camera 110, a slit lamp 120, a camera housing 130, a plurality of illumination source optics 140 and a processing system 150.

Figure 1A:
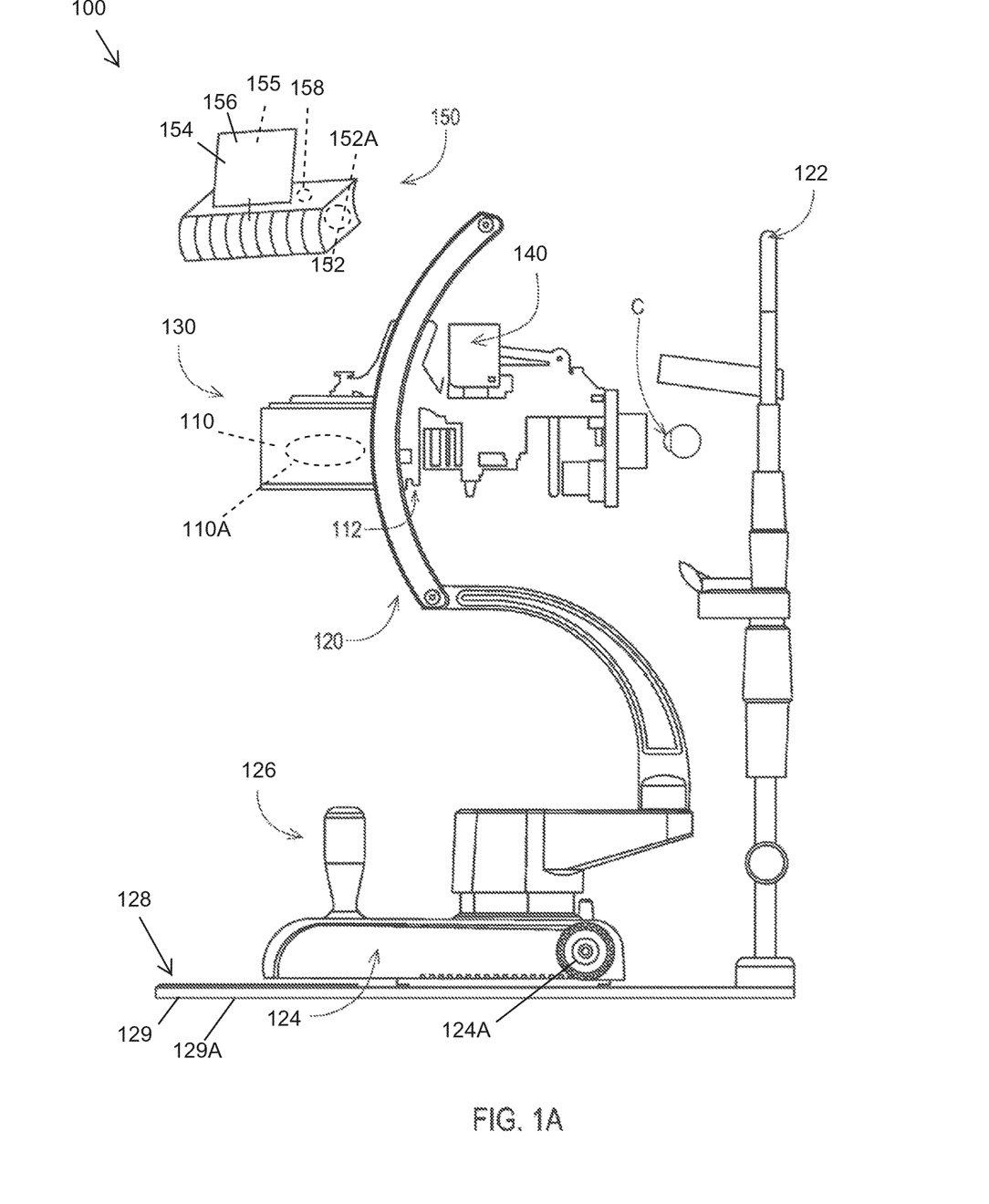
FIG. 1A illustrates a side view of an eye imaging apparatus, in accordance with one embodiment of the present invention.

The video camera 110 may include a plurality of video camera optics 112. The video camera 110 may be a digital camera 110A or any type of suitable camera to utilize with the eye imaging apparatus 100. The video camera 110 may record an image of an amyloid-beta plaque, an amyloid or an amyloid-beta peptide or other pathology or anatomical features in a patient user's eye or a patient user's brain or other suitable image. The eye imaging apparatus 100 may detect amyloid-beta plaque, amyloid or amyloid-beta peptide by a spectral signature. The eye imaging apparatus 100 may also perform maximum intensity projection and minimum intensity projection or MIP/MiniP.

The slit lamp chinrest 120 may include a head support 122, a movable base 124, a joystick 126 and a housing support 128. The head support 122 may be adapted to hold a patient user's chin and forehead in a fixed position. The head support 122 may be adapted to provide a plurality of elevation adjustments to provide a comfortable resting place to dispose a patient user's head. The camera housing 130 may be adapted to adjust the head support 122 in gross and fine increments utilizing the joystick 126. The movable base 124 may include one or more wheels 124A to move the eye imaging apparatus 100 along a ground surface 129 such as a floor 129A or other suitable ground surface. The illumination source optics 140 and video camera optics 112 may control focus, resolution and other suitable optics operations of the camera housing 130. The processing system 150 may be adapted to control the operations of the eye imaging apparatus 100. The processing system 150 may include a memory system 152 and an observation video monitor 154 which may be a personal computer monitor 156, as well as the slit lamp chinrest 120 and the joystick 126. The observation video monitor 154 may have high-resolution color graphics capability appropriate to display the patient user's eye or the patient user's brain images of the patient user to analyze.

The processing system 150 may be a relatively compact computer, an embedded computer or a tablet computer of relatively high processing power utilizing an operating system 158 and having one or more standardized card slots interface peripheral equipment such as one or more memory cards, a video board, a printer and a monitor. The processing system 150 may include a non-transitory storage media 152A residing on the memory system 152. A digitizing board 155 may accept a digital file or video input from the video camera 110 and function as a frame grabber or a display. When activated by the processing system 150, the digitizing board 155 may collect video and/or digital data and images from the video camera 110 instantly and store the collected video and/or digital data and images into digital data. The digital data produced may be stored in the memory system 152 and may be made available to the processing system 150 to analyze.

Figure 1B:
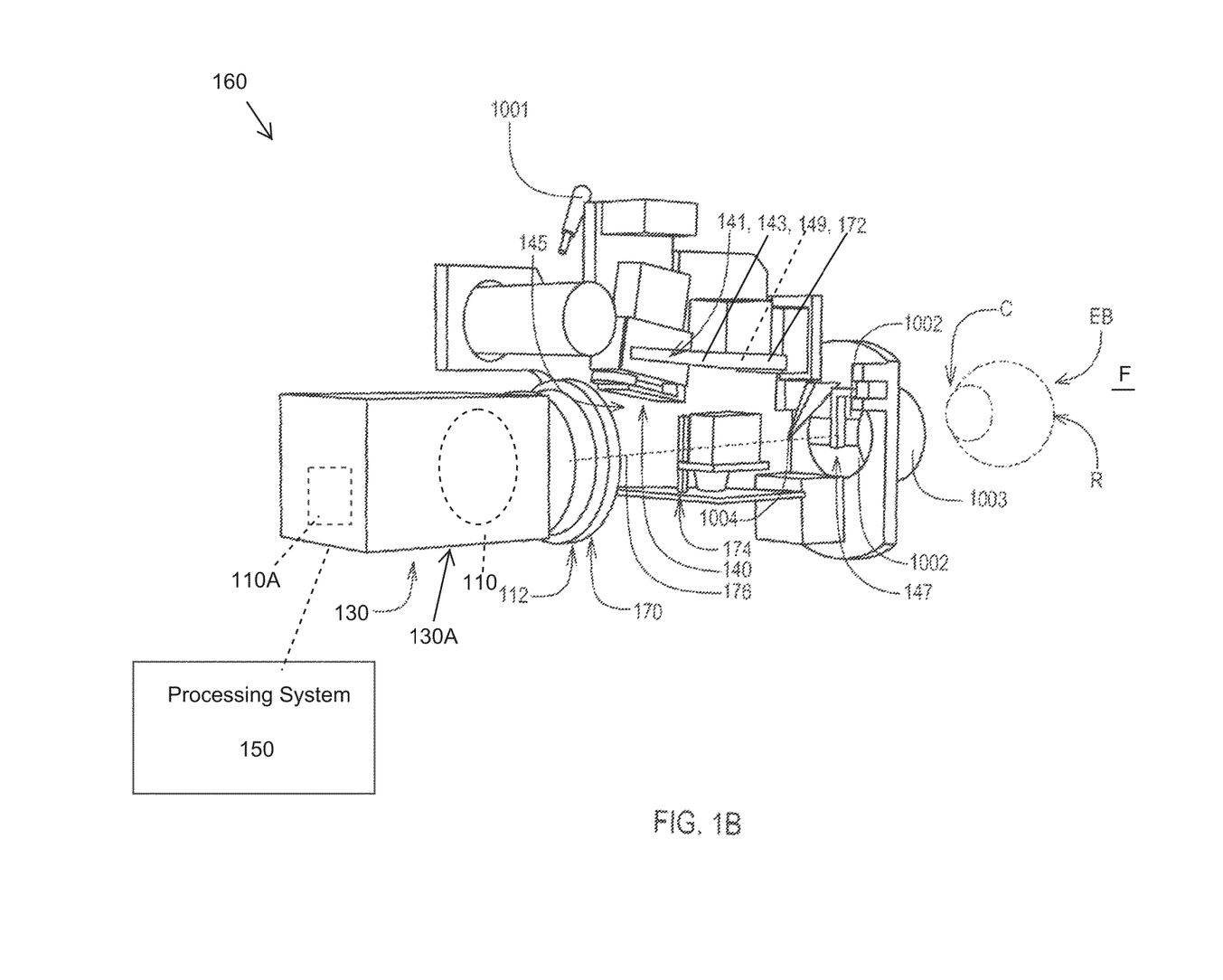
FIG. 1B illustrates a side perspective view of a camera assembly, in accordance with one embodiment of the present invention.

FIG. 1B illustrates a side perspective view of a camera assembly 160, in accordance with one embodiment of the present invention. The camera assembly 160 may include a camera housing 130, a video camera 110, a plurality of observation optics 112 and a lamp 141.

The camera housing 130 may contain one or more video camera illumination sources 110A, a plurality of illumination source optics 140 and may be adjacent to a patient user's eyeball EB with a cornea C and a patient user's retina R. The camera housing 130 may have a rectangular shape 130A or other suitable shape. The camera housing 130 may be provided without one or more forward protruding parts, which prevents accidental direct contact of any part of the eye imaging apparatus 100 with the patient user's cornea C or the patient user's face F during movement of the camera housing 130 adapted to the patient user's eyes. The camera housing 130 may be adapted to accomplish examination and image capture without contact with the patient user's cornea C. The camera housing 130 and the illumination source optics 140 may be adapted to maintain distance away from the cornea C, increasing patient user comfort while testing may be performed. A flexible interface such as a rubber cup (FIG. 1C, 180) may be provided between the camera housing 130 and the patient user's eyeball EB. The illumination source optics 140, the camera optics 112 and the video camera 110 in the camera housing 130 may provide a high degree of accessibility. The eye imaging apparatus 100 may include one camera housing 130 to allow an affordable design. Additionally, the eye imaging apparatus 100 in contrast to a fundus camera may be adapted to observation and image capture to provide a shorter and more efficient optical pathway. The illumination source optics 140 and the camera optics 112 may reduce production costs and permit greater ease of utilization by an operator user. The eye imaging apparatus 100 may allow imaging through a relatively smaller pupil in contrast to a fundus camera.

The video camera 110 may be relatively compact and incorporate a color or monochrome charge coupled device or CCD, a complementary metal-oxide-semiconductor or CMOS or a multi/hyper-spectral image sensor. The focus of the patient user may also be achieved by focus of internal optical elements of the digital camera. A lens contained inside the video camera 110 may be focused automatically or manually by observing the image displayed on an observation video monitor. Alternatively, an electronic auto-focusing control system may be automatically provided by adjusting the focus of the lens inside the video camera 110. The video camera 110 may also contain a monochrome or color CCD or CMOS sensor (not shown).

The observation optics 112 associated with the video camera 110 may include a lens 170, an observation aperture 172 and a filter 174. The observation aperture 172 and the filter 174 may transmit light reflected from the patient user's retina R to the lens 170 and to the video camera 110. The filter 174 may be an infrared stepping filter or other suitable filter to allow other imaging procedures which improves the contrast of the image seen by the video camera 110. Indocyanine green angiography, color fundus photography, autofluorescence, fluorescein angiography, curcumin fluorescence imaging or other suitable filter sets may be utilized by the eye imaging apparatus 100. The filters 174 may be adapted to rotate in and out of a view of an axis of the video camera 110 according to the function being performed. The rotation may be accomplished manually or by the processing system's servo control.

The illumination source optics 140 may project light onto the patient user's retina R, at an angle to a central axis 176 of the lens 170 of the video camera 110. The illumination source optics 140 may include a lamp 141, a lamp lens group 143, a mirror 145 and a projection aperture 172. A control device 1001 may be adapted to adjust the intensity and position of the lamp 141, either manually or under the control of the processing system 150. The control device 1001 may also be utilized to sequentially control multiple lamps 141, one or more shifting optical elements (not shown), a plurality of flipping masks 147, a Light Emitting Diode or LED flipping internal fixation pointer 1004 and an image capture trigger (not shown).

The lamp 141 may generate light that passes through an aperture 149 and the lamp lens group 143 that typically has two lenses. The lamp lens group 143 may concentrate the light from the lamp 141. The lamp lens group 143 may include a single aspheric lens. The light from the lamp 141 may then be deflected by the mirror 145, which may be placed at a critical pitch angle adapted to the video camera 110 and the projection optics 112. The light from the lamp 141 may pass from the mirror 145 past the flipping mask 147 which concentrates the light. The light from the lamp 141 may then pass through a plurality of small pupil masks 1002. The light from the lamp 141 may then pass through the objective lens 1003. The light from the lamp 141 may then pass past a user's cornea C and may be projected onto a patient user's retina R.

All of the masks and apertures utilized, such as the flipping mask 147 and a first aperture 149 and a second aperture 1002 may be aligned and corresponding sized apertures. Although the lamp 141 has been described as an LED lamp, the lamp 141 may be any source of radiant energy. The lamp 141 may be an infrared illumination source and the specifications of filter 174 may be adapted to pass the wavelength of the lamp 141. Infrared illumination may be particularly desirable to align prior to acquiring images without the problems generated by lack of pupil dilation. The image may be captured in a relatively dark room utilizing infrared illumination, so that the patient user's eye being imaged may be naturally dilated.

Figure 1C:
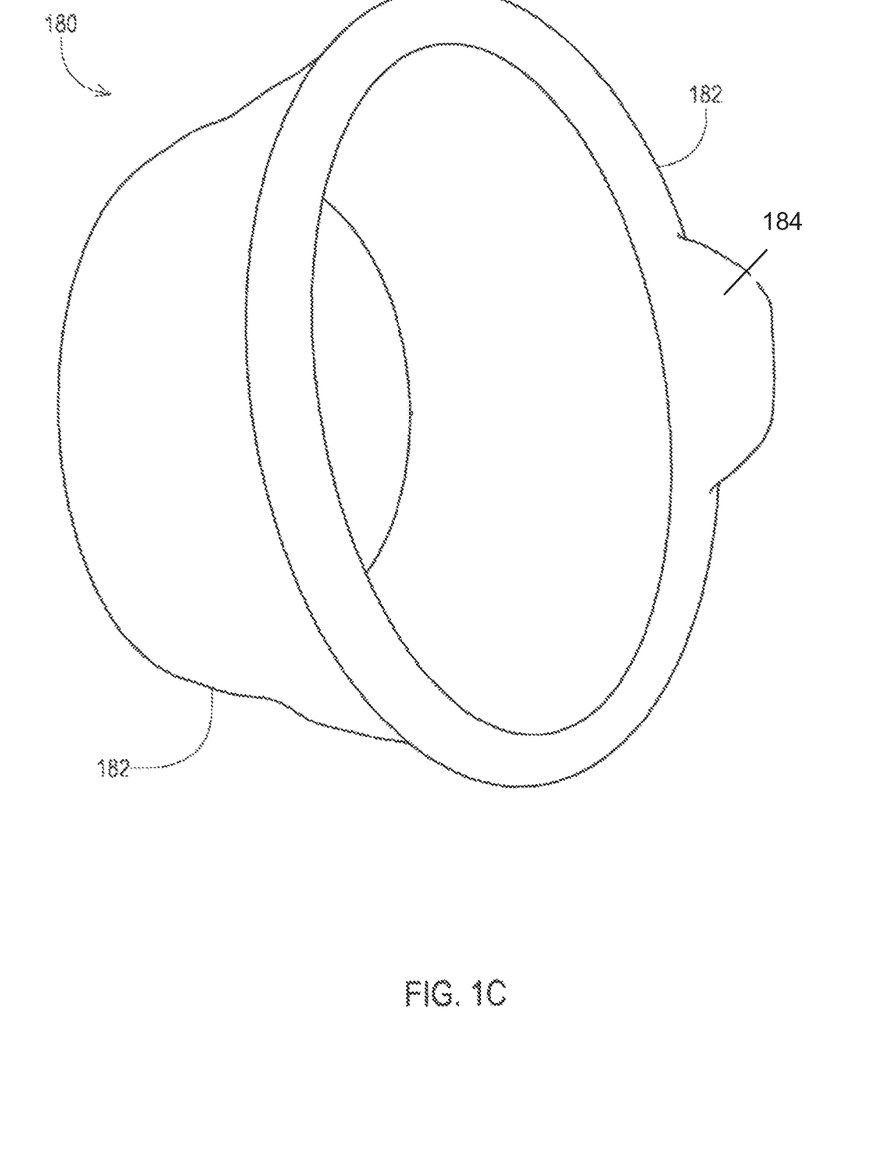
FIG. 1C illustrates a side perspective view of an eyecup, in accordance with one embodiment of the present invention.

The processing system 150 may turn a light source on and off in synchronization with image capture under each condition, which is further described in FIG. 1C. In another embodiment which addresses the problems caused by lack of pupil dilation during imaging, the lamp 141 may be strobed in full color, red free, near infrared reflectance or NIR or other wavelength based on imaging procedure desired during image acquisition rather than being kept on constantly, thereby preventing energy from the lamp 141 from narrowing a user's pupil prior to image capture. Because of the design of the illumination source optics 140 and the capabilities of the image processing and analysis non-transitory storage media, useful digital image data from each image may be collected with minimum user's pupil dilation. Specifically, the patient user's pupils being imaged may have a diameter of as little as approximately two millimeters. The illumination source optics 140 may project light onto the patient user's retina R off axis from the observation path of the video camera 110. Another embodiment may place an adjustable mask 1002 adjacent to the objective lens 1003 that may be adapted to adjust the patient user's pupil to optimize a digital image when the patient user's pupil may be relatively small.

FIG. 1C illustrates a side perspective view of an eyecup 180, in accordance with one embodiment of the present invention. The eyecup 180 may provide an interface between the camera housing (FIG. 1A, 130) and the patient user's eye that protrudes outward from a perimeter 182 to hold a patient user's eye lids open. The eyecup 180 may protrude outward from the perimeter 182 at an approximate ten percent increase at the approximate range of zero degrees to one hundred and eighty degrees on the perimeter 182. The eyecup 180 may include a grasping tab 184 disposed on the perimeter 182 to facilitate grasping the eyecup 180. The eyecup 180 may be made of rubber or other suitable material.

Figure 1D:
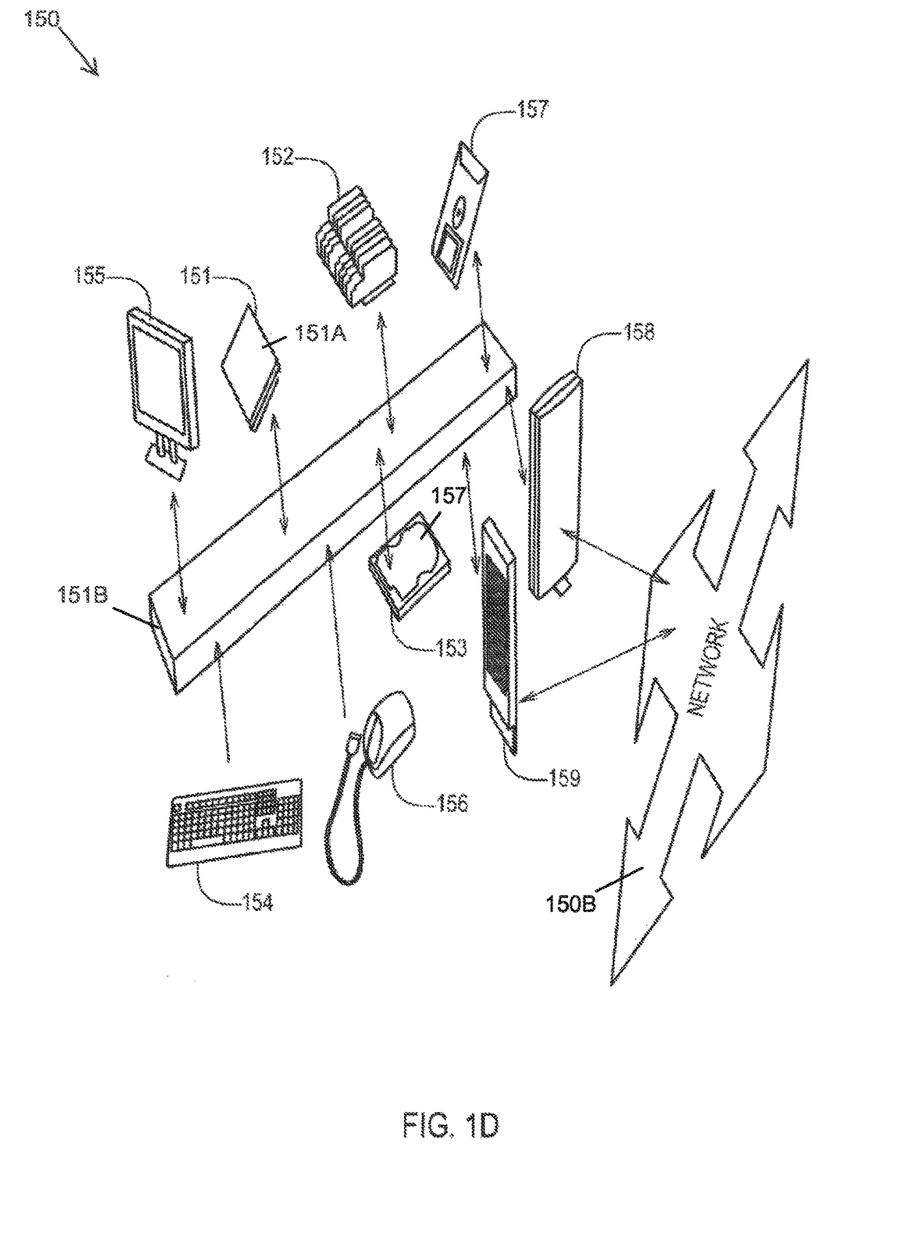
FIG. 1D is an exploded perspective view of a processing system, in accordance with one embodiment of the present invention.

FIG. 1D is an exploded perspective view of a processing system 150, in accordance with one embodiment of the present invention. The processing system 150 includes a processing unit 151 such as a CPU 151A or other suitable processing unit connected by a bus 151B to a random access memory or RAM 152, a storage device 153, a keyboard 154, a display 155 and a mouse 156. In addition, there may be a non-transitory storage media 157 that may store digital data generated from the processing unit 151. The processing system 150 may be a personal computer operating on an operating system such as a MICROSOFT WINDOWS®, LINUX®, MACINTOSH® or other suitable operating system. The processing system 150 may also be utilized on a laptop computer, a cell phone, a personal digital assistant or PDA, a tablet computer or other suitable device. The processing system 150 may also be utilized in combination with a wireless modem 158 or a network interface card 159 to access a communications network 150B such as the Internet or other suitable communications network.

Any combination of one or more computer usable or computer readable mediums may be utilized. Specific examples of the computer-readable medium may include a non-transitory storage media, a hard disk, a random access memory or RAM, a read-only memory or ROM, an erasable programmable read-only memory or EPROM, or flash memory or a portable compact disc read-only memory or CD-ROM. A computer-usable or computer-readable medium may be any medium that may be utilized by or in combination with the eye imaging apparatus. The program code may execute entirely on a user's computer, partly on the user's computer, as a stand-alone software package, partly on the user's computer and partly on a remote computer or entirely on the remote computer or server.

These computer program instructions may also be stored in a computer readable medium such as a non-transitory storage media that may direct a computer or other programmable data processing apparatus to function in a particular manner.

The computer program instruction may also be loaded onto a computer or other programmable data processing apparatus to cause a series of operational steps to be performed on the computer or other programmable apparatus to produce a computer implemented process such that the instructions which execute on the computer or other programmable apparatus provide processes to implement any suitable functions.

Figure 2:
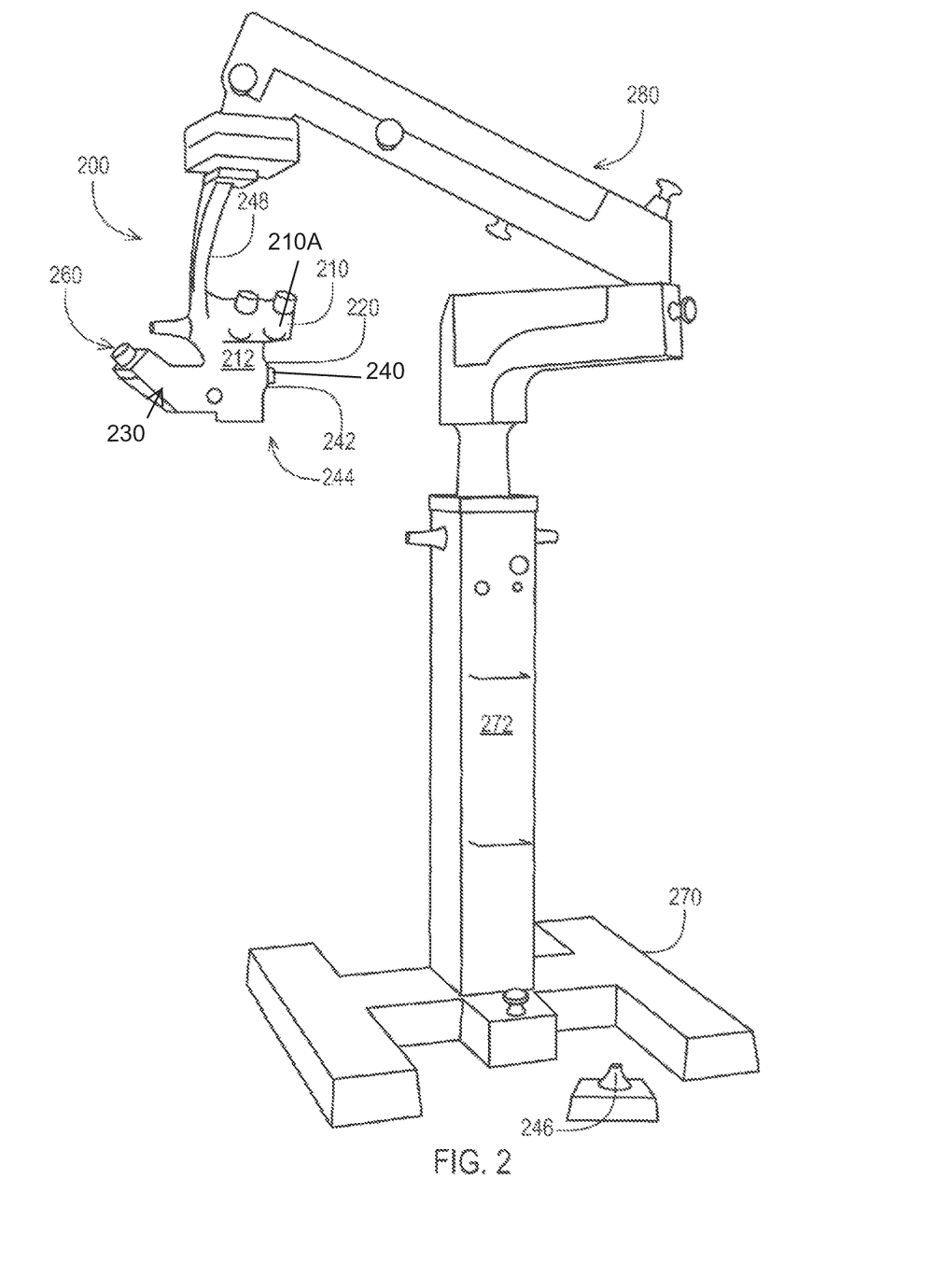
FIG. 2 illustrates a side perspective view of an eye imaging apparatus utilized in combination with a microscope, in accordance with one embodiment of the present invention.

FIG. 2 illustrates a side perspective view of an eye imaging apparatus 200 utilized in combination with a microscope 260, in accordance with one embodiment of the present invention. The eye imaging apparatus 200 may include a microscope 260 and may be provided without a processing system (FIG. 1, 150).

The eye imaging apparatus 200 includes a video camera 210, a plurality of video camera optics 212, a camera housing 220, a microscope assembly 230, a plurality of illumination source optics 240 and a floor base 270. The video camera 210 may include a digital video camera 210A. The microscope assembly 230 may include a head support 242, a movable base 244 and a housing support 248. The camera housing 220 may be mounted on a microscope assembly 230. The camera housing 220 may be adapted to adjust the head support 242 in gross and fine increments utilizing a joystick 246. The microscope 260 may be any suitable microscope that may be utilized in combination with the video camera 210 to produce a magnified view of a patient user's eye image. The floor base 270 may include a stem 272 extending from the floor base 270 coupled to a movable extending arm 280. The movable extending arm 280 may be coupled to the housing support 248.

In one embodiment of the eye imaging apparatus, OCT data may be presented with traditional OCT display modalities and/or en face to produce a plurality of retinal images.

In one embodiment of the eye imaging apparatus, OCT may be performed utilizing a plurality of specific wavelengths that allow visualization of amyloid in the patient user's retina and the patient user's brain. A plurality of OCT data sets may be obtained and analysis may be performed to identify a plurality of spectral signature components of the amyloid. These spectral components that correspond to the amyloid may be subsequently displayed in the OCT data sets that include an en face presentation. Spectral signal characteristics may be combined with other specific spectral components to render traditional OCT data sets in combination with the amyloid spectral data set.

In another embodiment of the eye imaging apparatus, a minimum threshold technique in combination with an adaptive spectral windowing technique may be applied to the data sets to render visualization of previous unseen features in the OCT data sets. In another embodiment of the eye imaging apparatus, the adaptive spectral windowing technique may be applied to not only amyloid but also other pathology and also anatomical features of the patient user's retina.

In another embodiment of the eye imaging apparatus, an OCT device may be operated at a plurality of different and specific spectral wavelengths to tease out desired signature and information.

In another embodiment of the eye imaging apparatus, the eye imaging apparatus may utilize multispectral imaging to image amyloid and other retinal pathology and features without utilization of one or more dyes or contrast agents. In another embodiment of the eye imaging apparatus, the multispectral imaging may be accomplished via optical multispectral imaging and/or autofluorescence techniques in which the specific amyloid signal may be identified and presented.

In another embodiment of the eye imaging apparatus, curcumin which binds to an amyloid may be utilized as a contrast agent in combination with OCT to discreetly identify the amyloid. In another embodiment of the eye imaging apparatus, curcumin may be utilized as a contrast agent in combination with multispectral optical and/or autofluorescence imaging to discreetly identify amyloid in the patient user's retina.

Another embodiment of the eye imaging apparatus includes diagnosing macular degeneration and other eye diseases in a mammal user that administers a fluorescent marker to the mammal user to stain a plurality of A beta peptides, imaging the patient user's retina with optical coherence tomography OCT, examining the data sets to stain A beta peptides and diagnosing the mammal user as having macular degeneration or another eye disease if stained A beta peptides may be present.

Another embodiment of the eye imaging apparatus utilizes a fluorescent marker selected from the group including but not limited to diarylheptanoid or curcumin, diarylheptanoid or curcumin derivatives, methylated dehydrothiotoluidine with sulfonic acid or Thioflavin S, methylated dehydrothiotoluidine with sulfonic acid or Thioflavin S derivatives, methylated dehydrothiotoluidine with methanol in presence of hydrochloric acid or Thioflavin T, methylated dehydrothiotoluidine with methanol in presence of hydrochloric acid or Thioflavin T derivatives, sodium salt of 3,3'-([1,1'-biphenyl]-4,4'-diyl)bis(4-aminonaphthalene-1-sulfonic acid) or Congo Red, one or more sodium salts of 3,3'-([1,1'-biphenyl]-4,4'-diyl)bis(4-aminonaphthalene-1-sulfonic acid) or Congo Red derivatives, 2,5-Bis(2-(4-hydroxyphenyl)vinyl)anisole or methoxy-X04, a radioactive analog of methylated dehydrothiotoluidine with methanol in presence of hydrochloric acid or Pittsburgh Compound B or PiB, Diazodinitrophenol or DDNP or 4,4'-Bis(3-carboxy-4-hydroxyphenylazo)biphenyl disodium salt or Chrysamine-G and any combinations thereof.

In another embodiment of the eye imaging apparatus, an OCT system may include a spectrometer, a fluorescence microscope, a stereomicroscope, a mercury arc lamp, a variable wavelength light source, a xenon arc lamp, an LED light, a tunable light source, a swept source, a charge coupled device or CCD gated camera, a color digital camera, an acoustic-optic tunable filter-based spectral image acquisition system, a plurality of adaptive optics, an imaging non-transitory storage media and any combinations thereof.

Another embodiment of the eye imaging apparatus may be to prognose macular degeneration and other eye disease in a mammal user that includes identification of A beta peptides, imaging the patient user's retina with OCT and/or multispectral imaging/autofluorescence, examining the images of A beta peptides, quantitating the increase/decrease of A beta peptides in the patient user's retina, as compared to a prior diagnosis and rendering a prognosis based upon the level of A beta peptides in the patient user's retina including but not limited to number, area and volume.

Another embodiment of the eye imaging apparatus may be to prognose macular degeneration and other eye disease in a mammal user that includes identification of A beta peptides, imaging the patient user's retina with OCT and/or multispectral imaging/autofluorescence, examining the images of A beta Peptides, quantitating the increase/decrease of A beta peptides in the patient user's retina, as compared to a prior diagnosis in combination with a normative database and rendering a prognosis based upon a level of A beta peptides in the patient user's retina including but not limited to number, area and volume.

Another embodiment of the eye imaging apparatus may be to prognose traumatic patient user's brain injury and other neurodegenerative disease in a mammal user that includes identification of A beta peptides, imaging the patient user's retina with OCT and/or multispectral imaging/autofluorescence, examining the images of A beta Peptides, quantitating the increase/decrease of A beta peptides in the patient user's retina, as compared to a prior diagnosis in combination with a normative database and rendering a prognosis based upon a level of A beta peptides in the patient user's retina including but not limited to number, area and volume.

Another embodiment of the eye imaging apparatus may be to perform a Maximum/Minimum Intensity Projection or MIP/MiniP and/or in combination with other specific discreet spectral signatures on OCT and/or multispectral images of the identification of amyloid in the patient user's retina or the patient user's brain and other retinal features and pathology including but not limited to choroidal neovascularization. Maximum intensity projection or MIP and minimum intensity projection MiniP may be defined as volume rendering techniques in which suitable editing methods may be utilized to define a volume of interest or VOI. All of the image data set may be utilized or the volume may be confined to a region of interest or ROI.

In one embodiment of the eye imaging apparatus, only desired features may be included or excluded from the VOI and actual images may be generated by projecting the volume of interest into a viewing plane and displaying the maximum OCT numbers or MIP or the minimum OCT numbers or MiniP that may be encountered along the direction of the projection to ensure that optimum contrast may be produced between small, high-contrast structures and surrounding tissues.

Figure 3:
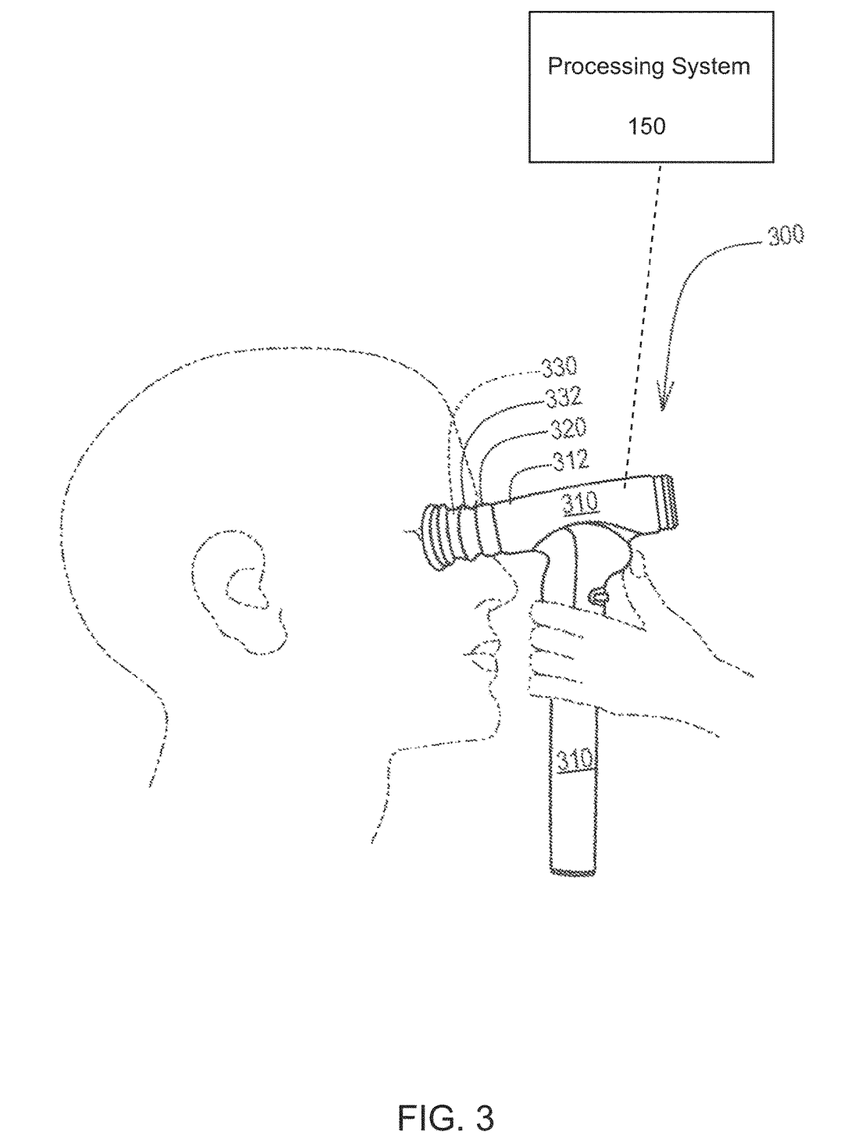
FIG. 3 illustrates a side view of a handheld imaging apparatus, in accordance with one embodiment of the present invention.

FIG. 3 illustrates a side view of a handheld imaging apparatus 300, in accordance with one embodiment of the present invention. The handheld imaging apparatus 300 may include all of the same components of the eye imaging apparatus 100 described in FIG. 1B and may not be utilized in combination with a microscope (FIG. 2, 260) but may be utilized with a processing system (FIG. 1A, 150). The handheld imaging apparatus 300 may utilize a hand-held housing 310 instead of a camera housing (FIG. 1A, 130), but utilizes all of the same optical and electrical components disposed within the hand-held housing 310.

The handheld imaging apparatus 300 may also utilize a flexible eyecup 320 that may be coupled to the hand-held apparatus 300 to produce an image of a handheld imaging apparatus 300, or be utilized as a disposable flexible eyecup that couples to the end 312 of the apparatus to produce an image of an patient user's eye to utilize on each patient user. The flexible eyecup 320 may be made of baffles 332 such as rubber, plastic, or any type of suitable material that gently surrounds the patient user's eye to create a darkened environment and may also be utilized to hold the patient user's eyelids open. The flexible eyecup 320 may have an angular internal spring 330 that holds the patient user's eyelids open. The baffles 332 may be flexible to allow adjustable and proper positioning around the patient user's eye.

Figure 4:
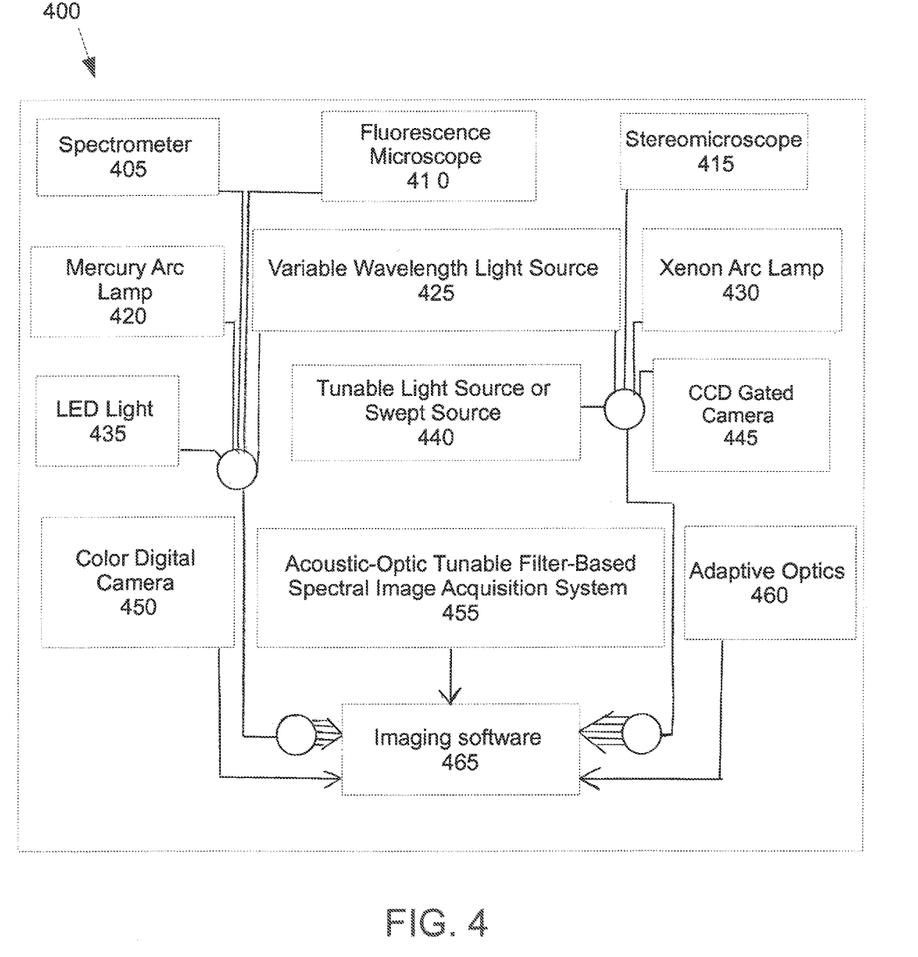
FIG. 4 is a block diagram of various components that may be utilized in combination with an eye imaging apparatus, in accordance with one embodiment of the present invention.

FIG. 4 is a block diagram of a plurality of components 400 that may be utilized in combination with an eye imaging apparatus (FIG. 1, 100), in accordance with one embodiment of the present invention. These components 400 are selected from the group consisting of a spectrometer 405, a fluorescence microscope 410, a stereomicroscope 415, a mercury arc lamp 420, a variable wavelength light source 425, a xenon arc lamp 430, an LED light 435, a tunable light source or swept source 440, a CCD gated camera 445, a color digital camera 450, an acoustic-optic tunable filter-based spectral image acquisition system 455, a plurality of adaptive optics 460, imaging non-transitory storage media 465 and any combinations thereof.

The eye imaging apparatus 100 may be utilized in combination with one or more contrasting agents that are selected from the group consisting of diarylheptanoid or curcumin, diarylheptanoid or curcumin derivatives, methylated dehydrothiotoluidine with sulfonic acid or Thioflavin S, one or more methylated dehydrothiotoluidine with sulfonic acid or Thioflavin S derivatives, methylation of dehydrothiotoluidine with methanol in presence of hydrochloric acid or Thioflavin T, one or more methylation of dehydrothiotoluidine with methanol in presence of hydrochloric acid or Thioflavin T derivatives, sodium salt of 3,3'-([1,1'-biphenyl]-4,4'-diyl)bis(4-aminonaphthalene-1-sulfonic acid) or Congo Red, one or more sodium salts of 3,3'-([1,1'-biphenyl]-4,4'-diyl)bis(4-aminonaphthalene-1-sulfonic acid) or Congo Red derivatives, 2,5-Bis(2-(4-hydroxyphenyl)vinyl)anisole or methoxy-X04, a radioactive analog of methylation of dehydrothiotoluidine with methanol in presence of hydrochloric acid or Pittsburgh Compound B or PiB, Diazodinitrophenol or DDNP or 4,4'-Bis(3-carboxy-4-hydroxyphenylazo)biphenyl disodium salt or Chrysamine-G and any combinations thereof.

While the present invention has been related in terms of the foregoing embodiments, those skilled in the art will recognize that the invention is not limited to the embodiments described. The present invention may be practiced with modification and alteration within the spirit and scope of the appended claims. Thus, the description is to be regarded as illustrative instead of restrictive on the present invention.

The invention claimed is:

1. An eye imaging apparatus, comprising:
a digital video camera having a plurality of video camera optics, wherein the digital video camera records an image of an amyloid-beta plaque, an amyloid or an amyloid-beta peptide in a patient user's eye or in a patient user's brain;
a slit lamp chinrest adapted to hold a patient user's chin and forehead in a fixed position, the slit lamp chinrest includes a head support, a movable base, a joystick and a housing support;
a camera assembly having a camera housing, the digital video camera, a plurality of observation optics and a lamp;
a plurality of illumination source optics controlling focus and resolution of the camera housing; and
a processing system having a memory system and an observation video monitor, the observation video monitor having high-resolution color graphics capability to display the patient user's eye image or the patient user's brain image to be analyzed, the processing system also having a digitizing board to collect video and digital data and images from the digital video camera instantly and store the collected video and digital data and images into digital data in the memory system and the collected video and digital data and images are available to the processing system to analyze.

2. The eye imaging apparatus according to claim 1, wherein the digital video camera incorporates a color or monochrome charge coupled device or a complementary metal oxide semiconductor.

3. The eye imaging apparatus according to claim 1, wherein the head support is adapted to provide a plurality of elevation adjustments to provide a comfortable resting place to dispose a patient user's head.

4. The eye imaging apparatus according to claim 1, wherein the movable base includes one or more wheels to move the eye imaging apparatus along a ground surface.

5. The eye imaging apparatus according to claim 1, wherein the camera housing is adapted to adjust the head support in gross and fine increments utilizing the joystick.

6. The eye imaging apparatus according to claim 1, further comprising a rubber cup provided between the camera housing and a patient user's eyeball.

7. The eye imaging apparatus according to claim 1, wherein the eye imaging apparatus is utilized in combination with one or more contrasting agents that are selected from the group consisting of diarylheptanoid, one or more diarylheptanoid derivatives, methylated dehydrothiotoluidine with sulfonic acid, one or more methylated dehydrothiotoluidine with sulfonic acid derivatives, methylation of dehydrothiotoluidine with methanol in presence of hydrochloric acid, one or more methylation of dehydrothiotoluidine with methanol in presence of hydrochloric acid derivatives, sodium salt of 3,3'-([1,1'-biphenyl]-4,4'-diyl)bis(4-aminonaphthalene-1-sulfonic acid), one or more sodium salts of 3,3'-([1,1'-biphenyl]-4,4'-diyl)bis(4-aminonaphthalene-1-sulfonic acid) derivatives, 2,5-Bis(2-(4-hydroxyphenyl)vinyl)anisole or methoxy-X04, a radioactive analog of methylation of dehydrothiotoluidine with methanol in presence of hydrochloric acid, Diazodinitrophenol or 4,4'-Bis(3-carboxy-4-hydroxyphenylazo)biphenyl disodium salt and any combinations thereof.

8. The eye imaging apparatus according to claim 6, wherein the camera housing is provided without one or more forward protruding parts, which prevents accidental direct contact of the eye imaging apparatus with the patient user's cornea or the patient user's face during movement of the camera housing.

9. The eye imaging apparatus according to claim 1, wherein the eye imaging apparatus detects the amyloid-beta plaque, the amyloid or the amyloid-beta peptide by a spectral signature.

10. The eye imaging apparatus according to claim 1, wherein the eye imaging apparatus performs maximum intensity projection and minimum intensity projection.

11. An eye imaging apparatus, comprising:
a digital video camera having a plurality of digital video camera optics controlling focus and resolution for obtaining digital video images;
a camera housing mounted on a microscope assembly, the microscope assembly having a head support, a movable base and a housing support, the camera housing adapted to adjust the head support in gross and fine increments utilizing a joystick and the camera housing having a plurality of illumination source optics;
a floor base including a stem extending from the floor base, the stem is coupled to a movable extending arm, the movable extending arm is coupled to the housing support; and
a microscope utilized in combination with the video camera, the microscope to produce a magnified view of a patient user's eye image.

12. The eye imaging apparatus according to claim 11, wherein the digital video camera incorporates a color or monochrome charge coupled device or a complementary metal oxide semiconductor.

13. The eye imaging apparatus according to claim 11, wherein the head support is adapted to provide a plurality of elevation adjustments to provide a comfortable resting place to dispose a patient user's head.

14. The eye imaging apparatus according to claim 11, wherein the movable base includes one or more wheels to move the eye imaging apparatus along a ground surface.

15. The eye imaging apparatus according to claim 11, wherein the camera housing is adapted to adjust the head support in gross and fine increments utilizing the joystick.

16. The eye imaging apparatus according to claim 11, wherein the eye imaging apparatus is utilized in combination with one or more contrasting agents that are selected from the group consisting of diarylheptanoid, one or more diarylheptanoid derivatives, methylated dehydrothiotoluidine with sulfonic acid, one or more methylated dehydrothiotoluidine with sulfonic acid derivatives, methylation of dehydrothiotoluidine with methanol in presence of hydrochloric acid, one or more methylation of dehydrothiotoluidine with methanol in presence of hydrochloric acid derivatives, sodium salt of 3,3'-([1,1'-biphenyl]-4,4'-diyl)bis(4-aminonaphthalene-1-sulfonic acid), one or more sodium salts of 3,3'-([1,1'-biphenyl]-4,4'-diyl)bis(4-aminonaphthalene-1-sulfonic acid) derivatives, 2,5-Bis(2-(4-hydroxyphenyl)vinyl)anisole or methoxy-X04, a radioactive analog of methylation of dehydrothiotoluidine with methanol in presence of hydrochloric acid, Diazodinitrophenol or 4,4'-Bis(3-carboxy-4-hydroxyphenylazo)biphenyl disodium salt and any combinations thereof.

17. The eye imaging apparatus according to claim 11, further comprising a rubber cup provided between the camera housing and a patient user's eyeball.

18. The eye imaging apparatus according to claim 11, wherein the camera housing is provided without one or more forward protruding parts, which prevents accidental direct contact of the eye imaging apparatus with the patient user's cornea or the patient user's face during movement of the camera housing.

19. The eye imaging apparatus according to claim 11, wherein the eye imaging apparatus detects an amyloid-beta plaque, a amyloid or an amyloid-beta peptide by a spectral signature.

20. The eye imaging apparatus according to claim 11, wherein the eye imaging apparatus performs maximum intensity projection and minimum intensity projection.

* * * * *